US008383663B2

(12) United States Patent
Alakhov et al.

(10) Patent No.: US 8,383,663 B2
(45) Date of Patent: *Feb. 26, 2013

(54) BENDAMUSTINE ANIONIC-CATIOINIC CYCLOPOLYSACCHARIDE COMPOSITIONS

(75) Inventors: Valery Alakhov, Ile Bizard (CA);
Grzegorz Pietrzynski, Montreal (CA);
Patel Kishore, Pierrefonds (CA);
Thomasz Popek, Pointe-Claire (CA)

(73) Assignee: Supratek Pharma Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/032,168

(22) Filed: Feb. 22, 2011

(65) Prior Publication Data

US 2012/0015995 A1      Jan. 19, 2012

Related U.S. Application Data

(60) Provisional application No. 61/399,855, filed on Jul. 19, 2010.

(51) Int. Cl.
*A61K 31/415* (2006.01)
(52) U.S. Cl. ........ 514/394; 514/393; 514/385; 514/359; 548/304.4; 548/302.7; 548/301.7; 548/300.1
(58) Field of Classification Search .................. None
See application file for complete search history.

(56) References Cited

U.S. PATENT DOCUMENTS

| | | | |
|---|---|---|---|
| 5,068,226 A | 11/1991 | Weinshenker et al. | |
| 5,324,750 A | 6/1994 | Lincoln et al. | |
| 6,407,079 B1 | 6/2002 | Mueller et al. | |
| 6,583,125 B2 | 6/2003 | Rubinfeld | |
| 6,624,141 B1 | 9/2003 | Yang et al. | |
| 2006/0128777 A1* | 6/2006 | Bendall et al. ............ | 514/394 |
| 2006/0159713 A1 | 7/2006 | Brittain et al. | |
| 2008/0299166 A1 | 12/2008 | Szente et al. | |

FOREIGN PATENT DOCUMENTS

| | | |
|---|---|---|
| CA | 2593582 A1 | 7/2006 |
| CA | 2593715 A1 | 8/2006 |
| CA | 2619676 A1 | 3/2007 |
| CA | 2679919 A1 | 9/2008 |
| CA | 2369451 C | 9/2009 |
| CN | 1846685 A | 10/2006 |
| CN | 101219113 A | 7/2008 |
| CN | 101606934 A | 12/2009 |
| CN | 101897977 A | 12/2010 |
| EP | 1250925 A2 | 10/2002 |
| WO | 9840069 A2 | 9/1998 |
| WO | 0119339 A1 | 3/2001 |
| WO | 03072141 A1 | 9/2003 |
| WO | 2010097700 A1 | 2/2010 |
| WO | 2010097700 A1 | 9/2010 |

OTHER PUBLICATIONS

"Recent Aspects of Cyclodextrin-Based Drug Delivery System" by Uekama et al., J. Incl. Phenom. Macro. Chem. 56, 3-8 (2006).*
"Recognition of Ionic Guests by Ionic beta-Cyclodextrin Derivatives" by Wenz et al., Chem. Eur. J. 14, 7202-11 (2008).*
Chatterji et al., "Kinetick of Chlorambucil Hydrolysis Using High-Pressure Liquid Chromatography", J Pharm Sci 71 (1):50-54 (1982).
Evjen, T.J., "Developments of Improved Bendamustin-Liposomes", Thesis for the degree of Master of Pharmacy, Department of Pharmaeutics and Biopharmaceutics, Institute of Pharmacy, Faculty of Medicine, University of Tormso (2007).
Haase et al., "Untersuchungen zur Plasmaeiweiβbindung von Bendamustin (Cytostasan(R)) and Ambazon", Z. Klin. Med. 45(14):1267-1271 (1990).
Maas et al., "Stabilitat von Bendamustinhydrochlorid in Infusionsloungen", Die Pharmazie 49:775-777 (1994).
Meyer-Losic et al., "DTS-108, A Novel Peptidic Prodrug fo SN38; in vivo Efficacy and Toxicokinetic Studies", Clin Cancer Res 14(7):2145-2153 (2008).
Pencheva et al., HPLC Study on the stability of bendamustine hydrochloride immobilized onto polyphosphoesters, J Pharm Biomed Anal (2008) doi:10.1016/j.pba.2008.09.001.
Preiss et al.,"Untersuchungen zur Pharmakokinetik von Bendamustin (Cytostasan(R)) am Menschem", Pharmazie 40:782-784 (1985).
Teichert et al., "Characterization of two phase I metabolites of bendamustine in human liver microsomes and in cancer patients treated with bendamustine hydrochloride", Cancer Chemother Pharmacol 59:759-770 (2007).
Brewster et al., "Cyclodextrins as pharmaceutical solubilizers", Advanced Drug Delivery Reviews 59:645-666 (2007).
Huang et al., "Pharmacokinetics, Efficacy, and Safety Evaluation of Docetaxel/Hydroxypropyl-Sulfobutyl-beta-Cyclodextrin Inclusion Complex" AAPS PharmSciTech, 12(2):665-672 (2011).
Luke et al., "Review of the Basic and Clinical Pharmacology of Sulfobutylether-b-Cyclodextrin (SBECD)", J.Pharm. Sci. 99(8):3291-3301 (2010).
Rajewski et al., "Pharmaceutical Applications of Cyclodextrins. 2. In Vivo Drug Delivery", Journal of Pharmaceutical Sciences 85(11):1142-1169 (1996).
Thiele et al., "Inclusion of chemotherapeutic agents in substituted b-cyclodextrin derivatives", J Incl Phenom Macrocycl Chem DOI 10.1007/s10847-010-9741-4.
Wang et al., "Sulfur, oxygen, and nitrogen mustards: stability and reactivity", Org. Biomol. Chem. 10:8786-8793 (2012). EC Safety Data Sheet in accordance with 91/155 EEC—Ribomustin(R) Bendamustin—The hybrid alkylating agent. Muntipharma Oncology.
TREANDA (bendamustine HCl)—Highlights of Prescribing Information.
Wenz, G. et al., "Recognition of Ionic Guests by Ionic Beta-Cyclodextrin Derivatives" Chemistry A European Journal, 14, 7202:7211 (2008).
Uekama, K et al., "Recent Aspect of Cyclodextrin-Based Drug Delivery System" Journal of Inclusion Phenomena and Macrocyclic Chemistry,56:3-8 ( 2006).

* cited by examiner

*Primary Examiner* — Brandon Fetterolf
*Assistant Examiner* — Theodore R West
(74) *Attorney, Agent, or Firm* — Porzio, Bromberg & Newman, P.C.

(57) ABSTRACT

The present invention is directed to pharmaceutical compositions including: (a) bendamustine, (b) a first charged cyclopolysaccharide, and (c) a stabilizing agent which is a second charged cyclopolysaccharide having a charge opposite to that of the first charged cyclopolysaccharide. The composition provides unexpectedly desirable stability in reactive environments such as plasma, coupled with unexpectedly desirable anticancer activity. The compositions are suitable for injection or infusion into patients in need for treatment with bendamustine.

6 Claims, No Drawings

BENDAMUSTINE ANIONIC-CATIOINIC CYCLOPOLYSACCHARIDE COMPOSITIONS

CROSS REFERENCE TO RELATED APPLICATION

This application claims the benefit of U.S. Provisional Patent Application No. 61/399,855, filed Jul. 19, 2010, the entirety of which is hereby incorporated by reference into this application.

FIELD OF THE INVENTION

The present invention is directed to a composition comprising:
(a) bendamustine;
(b) a first charged cyclopolysaccharide comprising at least one charged group; and
(c) a stabilizing agent which is a second charged cyclopolysaccharide having at least one charged group having a charge opposite to that of the first charged cyclopolysaccharide.

BACKGROUND OF THE INVENTION

Bendamustine, 4-[5-[bis(2-chloroethyl)amino]-1-methylbenzimidazol-2-yl]butanoic acid, is used in the treatment of leukemia and certain lymphomas. However, this compound has limited chemical stability in plasma, thereby requiring high or repeated doses in order to achieve a therapeutic effect. Thus there is a need for formulations of this drug which will exhibit increased stability.

Attempts have been made to increase the stability of bendamustine by complexing such molecule with polymeric materials. However, the approaches taken have only achieved marginal success. Thus, Pencheva et al; "HPLC study on the stability of bendamustine hydrochloride immobilized onto polyphosphoesters; J. Pharma. Biomed. Anal; (2008) attempted to improve the stability of bendamustine by complexing such compound with polyphosphoesters. However, FIG. 2 of such article shows that even the most stable complex decreases by one order of magnitude in about 45 minutes at pH 7.

Evjen; "Development of Improved Bendamustin-Liposomes"; Masters Thesis; University of Tromso (2007) employed dual asymmetric centrifugation to incorporate bendamustine into liposomes. According to Table 18 (on page 79), these formulations only provide a marginal increase of stability relative to free bendamustine (20 minutes half-life vs. 14 minutes half-life for free bendamustine when dispersed in a cell culture medium).

U.S. patent application Ser. No. 12/711,979 entitled "Bendamustine Cyclopolysaccharide Compositions" filed Feb. 24, 2010, describes certain bendamustine compositions comprising: (a) bendamustine, (b) a charged cyclopolysaccharide, and (c) a stabilizing agent having a charge opposite to that of the cyclopolysaccharide. Such compositions provide unexpectedly desirable stability coupled with unexpectedly desirable anticancer activity, which benefits are believed to be provided by the formation of a structure wherein the bendamustine is protected from the effects of reactive environment.

The composition of the present invention provides unexpectedly desirable stability in reactive environments such as plasma, coupled with unexpectedly desirable anticancer activity. The composition is suitable for injection or infusion into patients in need for treatment with bendamustine.

SUMMARY OF THE INVENTION

The present invention is directed to a composition comprising:
(a) bendamustine;
(b) a first charged cyclopolysaccharide comprising at least one charged group; and
(c) a stabilizing agent which is a second charged cyclopolysaccharide having at least one charged group having a charge opposite to that of the first charged cyclopolysaccharide.

It is believed that the structure described in U.S. patent application Ser. No. 12/711,979 ("the '979 application") involves the formation of a barrel-like structure wherein the bendamustine molecule is inserted into the hole of the cyclopolysaccharide, with the stabilizing agent acting as a "lid" to isolate the protruding portion of the molecule. While the '979 application discloses a variety of useful stabilizing agents, it does not disclose the use of charged cyclopolysaccharides as the stabilizing agent. Given the donut shape of such molecules, it is unexpected that such molecules could effectively function as an effective "lid" for the "barrel" created by the first charged cyclopolysaccharide.

There is a need for providing stabilizing agents that can effectively function with a first charged cyclopolysaccharide.

DETAILED DESCRIPTION

The present invention is directed to a composition comprising:
(a) bendamustine;
(b) a first charged cyclopolysaccharide comprising at least one charged group; and
(c) a stabilizing agent which is a second charged cyclopolysaccharide having at least one charged group having a charge opposite to that of the first charged cyclopolysaccharide.

As is employed herein, the term "bendamustine" refers to the compound 4-[5-[bis(2-chloroethyl)amino]-1-methylbenzimidazol-2-yl]butanoic acid, as well as to pharmaceutically acceptable salts thereof, including bendamustine hydrochloride.

Preferably, the proportion of bendamustine to the first charged cyclopolysaccharide, by weight, is between about 1:5000 and about 1:5; is more preferably between about 1:1000 and about 1:8; is even more preferably between about 1:500 and about 1:10 and most preferably between about 1:100 and about 1:10.

The stabilizing agent is typically present in a weight ratio to the first charged cyclopolysaccharide of between about 5:1 and about 1:1000; preferably of between about 1:4 and about 1:100.

Cyclopolysaccharides

The cyclopolysaccharides which can be employed in the practice of this invention include cyclodextrins, cyclomannins, cycloaltrins, cyclofructans and the like. In general, cyclopolysaccharides comprising between 6 and 8 sugar units are preferred.

Among the preferred cyclopolysaccharides is cyclodextrin. Cyclodextrin is a cyclic oligo-1-4-alpha-D-glucopiranose consisting of at least 6 sugar units. The most widely known are cyclodextrins containing six, seven or eight sugar units. Cyclodextrins containing six sugar units are known as alpha-cyclodextrins, those containing seven sugar units are known as beta-cyclodextrins and those consisting of eight sugar units are known as gamma-cyclodextrins. Particularly preferred cyclopolysaccharides are beta-cyclodextrins.

The cyclopolysaccharides employed in the practice of this invention, whether as the first cyclopolysaccharide or as the stabilizing agent, are charged cyclopolysaccharides. The term "charged cyclopolysaccharide" refers to a cyclopolysaccharide having one or more of its hydroxyl groups substituted with a charged moiety. Such moiety can itself be a charged group or it can comprise an organic moiety (e.g., a $C_1$-$C_6$ alkyl or $C_1$-$C_6$ alkyl ether moiety) substituted with one or more charged moieties.

In the event that the first charged cyclopolysaccharide is substituted with an anionic group, the stabilizing agent is a cationic cyclopolysaccharide. Conversely, in the event that the first charged cyclopolysaccharide is substituted with a cationic group, the stabilizing agent is an anionic cyclopolysaccharide.

Although the anionic cyclopolysaccharide can comprise any one or mixture of anionic groups, it is preferred that the anionic cyclopolysaccharide comprise a carboxyl, sulfonyl, or sulphate group. Preferred anionic cyclopolysaccharides include sulfobutyl ether beta-cyclodextrin, sodium carboxymethylated-beta-cyclodextrin, sodium O-phosphated-beta-cyclodextrin, succinyl-(2-hydroxy)propyl-beta-cyclodextrin, sodium sulfopropylated-beta-cyclodextrin, and sodium O-sulfated-beta-cyclodextrin. Sulfobutyl ether beta-cyclodextrin is particularly preferred.

Although the cationic cyclopolysaccharide can comprise any one or mixture of cationic groups, it is preferred that cationic cyclopolysaccharide comprise an amino, a guanidine or a quaternary ammonium group. Suitable amino-cyclodextrins which can be employed are amino-alpha-cyclodextrins, amino-beta-cyclodextrins, and amino-gamma-cyclodextrins, preferably having a substitution level of between about 4 and about 10. Preferred amino-cyclodextrins of this type include hexakis(6-amino-6-deoxy) alpha-cyclodextrin, heptakis(6-amino-6-deoxy) beta-cyclodextrin, octakis(6-amino-6-deoxy) gamma-cyclodextrin. Other cationic cyclopolysaccharides which can be employed include guanidino-cyclodextrins, preferably having a substitution level of between about 4 and about 10, such as heptakis(6-guanidino-6-deoxy) beta-cyclodextrin; alkylamino-cyclodextrins, preferably having a substitution level of between about 4 and about 10, such as 6-deoxy-6-(3-hydroxy)propylamino beta-cyclodextrin; and alkylammonium-cyclodextrins, preferably having a substitution level between 4 and 9, such as 2-hydroxy-N,N,N-trimethylpropanammonium-cyclodextrin.

Particularly preferred cationic polysaccharides include hexakis(6-amino-6-deoxy) alpha-cyclodextrin, heptakis(6-amino-6-deoxy) beta-cyclodextrin, octakis(6-amino-6-deoxy) gamma-cyclodextrin, heptakis(6-guanidino-6-deoxy) beta-cyclodextrin, octakis(6-guanidino-6-deoxy)-gamma-cyclodextrin, 2-hydroxy-N,N,N-trimethylpropanammonium-cyclodextrin and 6-deoxy-6-(3-hydroxy)propylamino beta-cyclodextrin.

In one particularly preferred embodiment of this invention, the first charged cyclopolysaccharide comprises sulfobutyl ether beta-cyclodextrin and the stabilizing agent comprises heptakis(6-amino-6-deoxy) beta-cyclodextrin.

Excipients

The compositions of this invention can further contain pharmaceutically acceptable excipients, such as sugars, polyalcohols, soluble polymers, salts and lipids.

Sugars and polyalcohols which can be employed include, without limitation, lactose, sucrose, mannitol, and sorbitol.

Illustrative of the soluble polymers which can be employed are polyoxyethylene, poloxamers, polyvinylpyrrolidone, and dextran.

Useful salts include, without limitation, sodium chloride, magnesium chloride, and calcium chloride.

Lipids which can be employed include, without limitation, fatty acids esters, glycolipids, phospholipids.

Preparation

The composition of this invention can be prepared by the dissolution of solid bendamustine in an aqueous solution of the first charged cyclopolysaccharide; or by mixing an aqueous solution of the first charged cyclopolysaccharide with an aqueous stock solution of bendamustine. Such resulting mixture is mixed and optionally subjected to the action of ultrasound waves to obtain homogenous and equilibrated aqueous solution. When the cyclopolysaccharide is a cyclodextrin, it is preferred that the aqueous solution of cyclodextrin used for the preparation of composition contains at least 4% of cyclodextrin; more preferably such solution contains at least 10% of cyclodextrin.

The stabilizing agent and excipient (if present) are preferably introduced to the composition by their addition to a pre-prepared aqueous homogenous and equilibrated solution of bendamustine with the first charged cyclopolysaccharide. Such agents can be added either as solids or as aqueous solutions.

Preferably, the final composition is filtered before use for injection.

The composition can be optionally freeze-dried to produce a solid material suitable for dissolution in injection media before its use. It is preferred that compositions comprising amines as stabilizing agents are freeze dried prior to the addition of such stabilizing agent, with such agent being introduced into the composition after reconstitution, shortly before use.

In one embodiment the composition of this invention is prepared by mixing the components and incubation.

In another embodiment the composition of this invention is prepared by mixing the components and applying ultrasound to the mixture.

In another embodiment the composition of this invention is prepared by mixing the components, incubation, and freeze-drying the product.

In a preferred embodiment the composition of this invention is prepared by mixing the components, applying ultrasound to the mixture, and freeze-drying the product.

The compositions of this invention demonstrate enhanced stability when introduced into plasma, both under in vitro and under in vivo conditions. Thus, such formulations will exhibit a half-life in plasma which is greater than that of non-formulated bendamustine; which half-life can be extended by at least about 10%, about 25%, about 50% or by about 100% or more.

In addition, the compositions of this invention exhibit unexpectedly improved activity against tumors relative to compositions comprising bendamustine and a cyclopolysaccharide; as well as relative to bendamustine alone.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

EXAMPLES

Example 1

Preparation of a Bendamustine Composition Comprising Sodium Sulfobutyl Ether β-Cyclodextrin (SBECD) and Heptakis(6-amino-6-deoxy)-beta-cyclodextrin hydrochloride (H6A)

Composition Comprising 2.5 mg/g Bendamustine HCl, 20% SBECD and 1% H6A

All operations were performed at room temperature. 3917 mg of water was added to 1000 mg of sodium sulfobutyl ether β-cyclodextrin and the mixture was mixed until the solid completely dissolved. 12.5 mg of bendamustine hydrochloride and 21 mg of mannitol were added to the solution and were mixed for 2 hours. 50 mg of H6A was added to the solution and was mixed for 15 minutes. The product solution was filtered through a 0.2 micrometer nylon filter.

Composition Comprising 2.5 mg/g Bendamustine HCl, 20% SBECD and 2% H6A

All operations were performed at room temperature. 3867 mg of water was added to 1000 mg of sodium sulfobutyl ether β-cyclodextrin and the mixture was mixed until the solid was completely dissolved. 12.5 mg of bendamustine hydrochloride and 21 mg of mannitol were added to the solution and were mixed for 2 hours. 100 mg of H6A was added to the solution and was mixed for 15 minutes. The product solution was filtered through a 0.2 micrometer nylon filter.

Composition Comprising 13 mg/g Bendamustine HCl, 20% SBECD and 1% H6A

All operations were performed at room temperature. 400 mg of water was added to 200 mg of sodium sulfobutyl ether β-cyclodextrin and the mixture was mixed until the solid was completely dissolved. 13 mg of bendamustine hydrochloride and 22.1 mg of mannitol were added to the solution and were mixed for 2 hours. 10 mg of H6A was dissolved in 355 mg of water, and the solution of H6A was added to a previously prepared solution of SBECD, bendamustine and mannitol, and was mixed for 15 minutes. The product solution was filtered through a 0.2 micrometer nylon filter.

Example 2

Pharmacokinetics of Bendamustine Dosed to Rats in a Composition Comprising Sodium Sulfobutyl Ether β-Cyclodextrin and heptakis(6-amino-6-deoxy-β-cyclodextrin).

The Tested Compositions:
 Control: 2.5 mg/g bendamustine hydrochloride, 4.25 mg/g of mannitol in 0.9% NaCl; dose of 10 mg/kg
 Composition 1: 2.5 mg/g bendamustine hydrochloride, 20% w/w sodium sulfobutyl ether β-cyclodextrin, 1% heptakis(6-amino-6-deoxy-β-cyclodextrin), 4.3 mg/g mannitol in water (prepared according to the procedure set forth in Example 1); dose of 10 mg/kg.
 Composition 2: 2.5 mg/g bendamustine hydrochloride, 20% w/w sodium sulfobutyl ether β-cyclodextrin, 2% heptakis(6-amino-6-deoxy-β-cyclodextrin), 4.3 mg/g mannitol in water (prepared according to the procedure set forth in Example 1); dose of 10 mg/kg.
 Composition A: 5 mg/mL bendamustine hydrochloride, 20% w/w sodium sulfobutyl ether β-cyclodextrin, 10.2 mg/g mannitol in water; dose of 10 mg/kg.

Animals:
 Female Sprague-Dawley rats (250-350 g). The animals were kept three per cage with an air filter cover under light (12 h light/dark cycle, light on at 06 h00) and controlled temperature 22° C.+/−1° C. All manipulations with the animals were performed under a sterilized laminar hood. The animals had ad libitum access to Purina mouse chow and water. The animals were fasted overnight and anesthetized, before dosing.

Dosing and Sampling:
 Bendamustine composition and control were administered intravenously to rats in tail vein. Blood samples were collected after time intervals of 5, 15, 30, 45 min, 1, 1.5, 2, 3 and 4 hrs post-injection. The rats were anesthetized by general inhalation of isoflurane. The blood samples were collected from the jugular vein with heparinized tube and kept on ice. The blood was immediately centrifuged, and plasma was separated. The plasma samples were immediately extracted.

Sample Extraction and Analysis:
 The plasma samples 0.100 mL were transferred to plastic tubes. The samples were extracted with 0.400 mL of 100 mM HCl in acetonitrile while being shaken vigorously for 30 seconds. The samples were centrifuged at 10000 RPM for 5 minutes. The supernatant was separated. The samples were frozen in dry ice and kept at −80 degree C. until HPLC analysis. The aliquots of 20 microliters were injected into HPLC for analysis.

The HPLC Conditions:
 C18 reversed phase column 50×4.6 mm, Symmetry/Shield 3.5 micrometer
 Column temperature 30° C.
 Flow rate 1.5 mL/min
 Injection volume 20 microliters
 Fluorescence detection at wavelengths: excitation 327 nm, emission 420 nm
 Mobile phase: Buffer A: 5% acetonitrile 0.1% TFA
 Buffer B: 90% acetonitrile 0.1% TFA
 Run time: 10 min The improved pharmacokinetic profiles of Bendamustine for the tested compositions, relative to the controls, is shown in Table 1 below.

TABLE 1

Concentration of bendamustine in rat plasma vs. time post injection

| Time [hours] | Control [ng/mL] Mean (SEM) | Composition 1 [ng/mL] Mean (SEM) | Composition 2 [ng/mL] Mean (SEM) | Composition A [ng/mL] Mean (SEM) |
|---|---|---|---|---|
| 0.08 | 6045 (388) | 4855 (724) | 6104 (432) | 5233 (143) |
| 0.25 | 2428 (250) | 2326 (270) | 4045 (338) | 1702 (217) |
| 0.5 | 520 (105) | 1428 (85) | 1964 (344) | 307 (73) |
| 0.75 | 145 (35) | 698 (73) | 902 (190) | 72 (25) |
| 1 | 48 (11) | 346 (22) | 625 (231) | 36 (17) |
| 1.5 | 8 (1) | 153 (11) | 221 (99) | 16 (10) |
| 2 | 2 (1) | 29 (4) | 94 (42) | 5 (4) |
| 3 | 0 (1) | 3 (1) | 18 (10) | 0 (0) |
| 4 | | 1 (0.4) | 3 (2) | |

SEM—standard error of mean

The above data demonstrates that the pharmacokinetics of bendamustine is greatly prolonged if the drug is dosed to subjects in the composition of the present invention. The above data further shows that the pharmacokinetics are also greatly increased by the addition of the H6A.

Example 3

Effect of bendamustine in a composition comprising sodium sulfobutyl ether β-cyclodextrin and heptakis(6-amino-6-deoxy-β-cyclodextrin) on growth of subcutaneous solid tumors of human breast carcinoma MDA-MB-231 cells in Balb/c mice.

Animal:

Balb/c mice aging 5 to 6 weeks were purchased from Charles River Canada Inc. The animals were kept 5 per cage with an air filter cover under light (12 light/dark cycle, light on at 6H00) and temperature (22°±1° C.)-controlled environment. All manipulations of animals were performed under a sterilized laminar. The animals had ad libitum access to Purina mouse chow (Pro Lab PMH 4018, Trademark of Agway, Syracuse, N.Y.) and water. These animal studies were conducted according to the "Guidelines for Care and Use of Experimental Animals".

Tumor Cell Culture:

Human breast cancer cells MDA-MB 231 were cultured in the appropriated culture medium. The cells were harvested in their logarithmic growth phase for the preparation of tumor implantation.

Tumor Cell Implantation:

MDA-MB-231 cells (5.0×10 5 cells per an injection) in culture medium with 30% Matrigel were subcutaneously inoculated at 2 sides of the flank of each animal. Nine to ten days after implantation, when tumor size reaches to 0.5 to 0.8 cm in the diameter, the animals were be randomly divided into groups, 5 animals per group. The treatments by intravenously injection were performed on day 1, 2, 13 and 14. The control group was treated with isotonic saline. The reference group was treated with 35 mg/kg dose of bendamustine HCl in water (7 mg/mL). The test group was treated with 60 mg/kg dose (equitoxic to the reference group treatment) of the composition of the present invention, comprising 13 mg/g bendamustine HCl, 20% SBECD and 1% H6A, and mannitol, prepared according to the procedure set forth in Example 1.

Efficacy Evaluation:

Subcutaneous solid tumor measurements were performed on the day of first injection and at 3- to 4-day intervals thereafter. Two largest perpendicular diameters of each tumor were measured with calipers and tumor size was estimated using formula $$TV = L \times W \times /2 \text{ where } TV: \text{tumor volume}; L: \text{length}; W: \text{width}.$$

The body weights of animals were also noted.
The results are presented in Table 2 below.

TABLE 2

Tumor weight after treatment in human breast carcinoma MDA-MB 231 s.c. solid tumors in nude mice

| Time [days] | Non-treated Control [g] Average (SEM) | Reference BM (35 mg/kg) [g] Average (SEM) | BM (60 mg/kg), 20% SBECD, 1% H6A [g] Average (SEM) |
|---|---|---|---|
| 0 | 0.108 (0.016) | 0.111 (0.013) | 0.111 (0.018) |
| 2 | 0.120 (0.015) | 0.123 (0.016) | 0.119 (0.019) |
| 5 | 0.135 (0.015) | 0.134 (0.015) | 0.117 (0.018) |
| 7 | 0.161 (0.019) | 0.146 (0.017) | 0.122 (0.02) |

TABLE 2-continued

Tumor weight after treatment in human breast carcinoma MDA-MB 231 s.c. solid tumors in nude mice

| Time [days] | Non-treated Control [g] Average (SEM) | Reference BM (35 mg/kg) [g] Average (SEM) | BM (60 mg/kg), 20% SBECD, 1% H6A [g] Average (SEM) |
|---|---|---|---|
| 9 | 0.192 (0.027) | 0.156 (0.017) | 0.130 (0.023) |
| 12 | 0.256 (0.039) | 0.174 (0.018) | 0.140 (0.024) |
| 14 | 0.318 (0.053) | 0.205 (0.021) | 0.140 (0.026) |
| 16 | 0.426 (0.07) | 0.228 (0.024) | 0.142 (0.026) |
| 19 | 0.522 (0.086) | 0.248 (0.035) | 0.138 (0.025) |
| 21 | 0.653 (0.103) | 0.272 (0.042) | 0.138 (0.026) |
| 23 | 0.809 (0.127) | 0.296 (0.047) | 0.141 (0.028) |

SEM—standard error of mean

The results show superior efficacy of the composition of the invention comprising SBECD and H6A, compared to an equitoxic dose of non-formulated bendamustine.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A composition comprising:
   (a) bendamustine;
   (b) a first charged cyclopolysaccharide selected from the group consisting of sulfobutyl ether beta-cyclodextrin, sodium sulfopropylated-beta-cyclodextrin, and sodium O-sulfated-beta-cyclodextrin; and
   (c) a stabilizing agent which is a second charged cyclopolysaccharide selected from the group consisting of heptakis(6-amino-6-deoxy) beta-cyclodextrin, heptakis (6-guanidino-6-deoxy) beta-cyclodextrin, and 6-deoxy-6-(3-hydroxy)propylamino beta-cyclodextrin.

2. The composition of claim 1 wherein component (b) is sulfobutyl ether beta-cyclodextrin.

3. The composition of claim 1 wherein component (c) is heptakis(6-amino-6-deoxy) beta-cyclodextrin.

4. The composition of claim 1 wherein the bendamustine is in the form of bendamustine hydrochloride.

5. A composition comprising:
   (a) bendamustine;
   (b) a first charged cyclopolysaccharide, said first charged cyclopolysaccharide is sulfobutyl ether beta-cyclodextrin; and
   (c) a stabilizing agent which is a second charged cyclopolysaccharide having a charge opposite to that of the first charged cyclopolysaccharide, said stabilizing agent is heptakis(6-amino-6-deoxy) beta-cyclodextrin.

6. The composition of claim 5 wherein the bendamustine is in the form of bendamustine hydrochloride.

* * * * *